United States Patent
Behl et al.

(10) Patent No.: US 6,337,998 B1
(45) Date of Patent: Jan. 8, 2002

(54) APPARATUS AND METHOD FOR TREATING TUMORS NEAR THE SURFACE OF AN ORGAN

(76) Inventors: Robert S. Behl, 361 Tioga Ct., Palo Alto, CA (US) 94036; Eben L. Kermit, 2066 Oakley Ave., Menlo Park, CA (US) 94025

( * ) Notice: Subject to any disclaimer, the term of this patent is extended or adjusted under 35 U.S.C. 154(b) by 0 days.

(21) Appl. No.: 09/354,379

(22) Filed: Jul. 14, 1999

Related U.S. Application Data

(63) Continuation-in-part of application No. 09/124,152, filed on Jul. 28, 1998.

(51) Int. Cl.[7] .................................................. A61F 2/00
(52) U.S. Cl. .......................... 607/101; 607/98; 607/113; 607/116; 606/41
(58) Field of Search ........................... 607/98, 101, 113, 607/115, 116; 606/32, 41, 45, 46, 47, 48, 49, 50; 128/898

(56) References Cited

U.S. PATENT DOCUMENTS

| | | |
|---|---|---|
| 1,814,791 A | 7/1931 | Ende |
| 3,991,770 A | 11/1976 | LeVeen |
| 4,016,886 A | 4/1977 | Doss et al. |
| 4,140,130 A | 2/1979 | Storm, III |
| 4,186,729 A | 2/1980 | Harrison |
| 4,448,198 A | 5/1984 | Turner |
| RE32,066 E | 1/1986 | LeVeen |
| 4,651,734 A | 3/1987 | Doss et al. |
| 4,969,468 A | 11/1990 | Byers et al. |
| 5,366,490 A | * 11/1994 | Edwards et al. ............... 607/99 |
| 5,383,917 A | * 1/1995 | Desai et al. .................. 607/101 |
| 5,472,441 A | 12/1995 | Edwards et al. |
| 5,536,267 A | 7/1996 | Edwards et al. |
| 5,562,720 A | 10/1996 | Stern et al. |
| 5,612,310 A | 3/1997 | Dewhirst et al. |
| 5,645,580 A | 7/1997 | Moaddeb et al. |
| 5,709,224 A | 1/1998 | Behl et al. |
| 5,728,143 A | 3/1998 | Gough et al. |
| 5,735,847 A | 4/1998 | Gough et al. |
| 5,769,846 A | 6/1998 | Edwards et al. |

FOREIGN PATENT DOCUMENTS

| | | |
|---|---|---|
| DE | 2 124 684 | 11/1972 |
| WO | WO 96/29946 | 10/1996 |
| WO | WO 97/06739 | 2/1997 |
| WO | WO 97/06740 | 2/1997 |
| WO | WO 97/06855 | 2/1997 |
| WO | WO 97/06857 | 2/1997 |
| WO | WO 99/04710 | 2/1999 |
| WO | WO 99/32041 | 7/1999 |

OTHER PUBLICATIONS

Rockwell, "The Medical Uses of Electricity", E.B. Trent & Co., New York, NY p.558 (1903).
Radio Therapeutics Corporation Brochure (002), LeVeen™ Needle Electrode (1998).

* cited by examiner

Primary Examiner—Linda C. M. Dvorak
Assistant Examiner—R. Kearney

(57) ABSTRACT

A system for treating a target region in tissue beneath a tissue surface comprises a probe for deploying an electrode array within the tissue and a surface electrode for engaging the tissue surface above the treatment site. Preferably, surface electrode includes a plurality of tissue-penetrating elements which advance into the tissue, and the surface electrode is removably attachable to the probe. The tissue may be treated in a monopolar fashion where the electrode array and surface electrode are attached to a common pole on an electrode surgical power supply and powered simultaneously or successively, or in a bipolar fashion where the electrode array and surface electrode are attached to opposite poles of the power supply. The systems are particularly useful for treating tumors and other tissue treatment regions which lie near the surface.

92 Claims, 8 Drawing Sheets

APPARATUS AND METHOD FOR TREATING TUMORS NEAR THE SURFACE OF AN ORGAN

This application is a continuation-in-part of application Ser. No. 09/124,152, filed on Jul. 28, 1998, the full disclosure of which is incorporated herein by reference.

BACKGROUND OF THE INVENTION

1. Field of the Invention

The present invention relates generally to the structure and use of radiofrequency electrosurgical apparatus for the treatment of solid tissue. More particularly, the present invention relates to an electrosurgical system having pairs of electrodes and electrode arrays which are deployed to treat large volumes of tissue, particularly for the treatment of tumors which lie close to the surface of an organ.

The delivery of radiofrequency energy to target regions within solid tissue is known for a variety of purposes. Of particular interest to the present invention, radiofrequency energy may be delivered to diseased regions in target tissue for the purpose of causing tissue necrosis. For example, the liver is a common depository for metastases of many primary cancers, such as cancers of the stomach, bowel, pancreas, kidney, and lung. Electrosurgical probes for deploying multiple electrodes have been designed for the treatment and necrosis of tumors in the liver and other solid tissues. See, for example, the LeVeen™ Needle Electrode available from RadioTherapeutics Corporation which is constructed generally in accord with published PCT application WO 96/29946.

The probes described in WO 96/29946 comprise a number of independent wire electrodes which are extended into tissue from the distal end of a cannula. The wire electrodes may then be energized in a monopolar or bipolar fashion to heat and necrose tissue within a defined volumetric region of target tissue. In order to assure that the target tissue is adequately treated and to limit damage to adjacent healthy tissues, it is desirable that the array formed by the wire electrodes within the tissue be precisely and uniformly defined. In particular, it is desirable that the independent wire electrodes be evenly and symmetrically spaced-apart so that heat is generated uniformly within the desired target tissue volume. Such uniform placement of the wire electrodes is difficult to achieve when the target tissue volume has non-uniform characteristics, such as density, tissue type, structure, and other discontinuities which could deflect the path of a wire as it is advanced through the tissue.

Of particular interest to the present invention, as recognized by the inventor herein, difficulties have arisen in using the multiple electrode arrangements of WO 96/29946 in treating tumors which lay at or near the surface of an organ, such as the liver. As illustrated in FIG. 1, a LeVeen™ Needle Electrode used for treating a tumor T near the surface S of a liver L can result in at least some of the tips of electrodes 12 emerging from the surface. Such exposure of the needle tips outside of the liver is disadvantageous in a number of respects. First, the presence of active electrodes outside of the confinement of the organ being treated subjects other tissue structures of the patient as well as the treating personnel to risk of accidental contact with the electrodes. Moreover, the presence of all or portions of particular electrodes outside of the tissue being treated can interfere with proper heating of the tissue and control of the power supply driving the electrodes. While it would be possible to further penetrate the needle electrode 10 into the liver tissue, such placement can damage excessive amounts of healthy liver. Moreover, the heating characteristics of the liver tissue near the surface will be different from those of liver tissue away from the surface, rendering proper treatment of the tumor tissue near the surface difficult even if the electrodes are not exposed above the surface.

In addition to difficulties in treating lesions near the surface of an organ, electrosurgical probes for performing large volume tissue ablation can have difficulty in treating highly vascularized tissues and/or tissue near a large blood vessel. In both cases, heat being introduced by the electrode can be rapidly carried away by the blood, making the heating and control of temperature in the tissue difficult.

For all of these reasons, it would be desirable to provide improved electrosurgical methods and systems for treating tumors which lie at or near the surface of an organ or tissue mass. It would be further desirable to provide such improved methods and systems which would be capable of improving beat transfer into and/or temperature uniformity of vascularized tissues where the heat can be taken away by blood flow. It would be particularly desirable if such methods and systems could lessen the risk of accidental exposure of the treating electrodes above the tissue surface. It would be further desirable if the methods and systems would enhance uniform treatment of the entire tumor mass, including those portions which lie near the surface of the organ being treated. Still further, it would be desirable if the methods and systems could achieve treatment of irregularly shaped tumors and tumors which extend from an organ surface to relatively deep within the organ. At least some of these objectives will be met by the invention of the present application.

2. Description of the Background Art

WO 96/29946 describes an electrosurgical probe having deployable electrode elements of the type described above. The LeVeen™ Needle Electrode constructed in accordance with the teachings of WO 96/229946 is available from Radio Therapeutics Corporation, assignee of the present application, and is illustrated in brochure RTC 002 published in 1998. Other electrosurgical devices having deployable electrodes are described in German Patent 2124684 (Stadelmayr); U.S. Pat. Nos. 5,472,441 (Edwards et al.); 5,536,267 (Edwards et al.); and 5,728,143 (Gough et al.); and PCT Publications WO 97/06739; WO 97/06740; WO 97/06855; and WO 97/06857. Medical electrodes having pins and other structures are shown in U.S. Pat. Nos. 3,991,770; Re. 32,066; 4,016,886; 4,140,130; 4,186,729; 4,448,198; 4,651,734; and 4,969,468. A skin surface treatment electrode for the removal of blemishes having a circular array of tissue-penetrating pins is described in Rockwell, *The Medical and Surgical Uses of Electricity*, E. B. Trent & Co., New York, 1903, at page 558. A cluster electrode comprising a plurality of electrodes projecting from a plate for insertion in tissue is described in WO 99/0410.

SUMMARY OF THE INVENTION

The present invention provides improved methods, systems, and kits for performing electrosurgical treatment of tumors and other disease conditions within body organs and other tissue masses. The methods, systems, and kits are particularly useful for treating tumors which lie at or near the surface of an organ, such as the liver, kidney, pancreas, stomach, spleen, particularly the liver. In a first aspect, the present invention relies on applying electrical energy, such as radiofrequency or other high frequency energy, to or between an internal tissue site and an external tissue site on the surface of the organ. The energy may be applied in a monopolar fashion where the internal and external sites are maintained at the same polarity and a dispersive or passive electrode disposed on the patient's skin is maintained at the opposite polarity. The high frequency energy can be applied simultaneously to both the internal and external sites, but will more usually be applied sequentially to one site and then to the other. The energy may also be applied in a bipolar fashion where the internal treatment site is maintained at one polarity and the external treatment site maintained at the opposite polarity. Monopolar treatment is advantageous in permitting formation of two fully formed lesions (necrosed regions) that can be overlapped to treat a desired region, but is disadvantageous since it requires use of a dispersive electrode. Bipolar treatment eliminates the need for a dispersive electrode and, by proper spacing, permits formation of a single, continuous lesion. Such approaches reduce the risk of passing internally deployed electrode(s) out through the surface of the body organ and enhances the uniform electrosurgical treatment of tissue between the internal and exterior treatment sites.

In a second aspect, the present invention provides for applying electrical energy, such as radiofrequency or other high frequency energy, to an internal tissue site while a cover is deployed over the tissue surface adjacent to the target region within the tissue which is being treated. The cover may comprise electrode(s) as described above. Alternatively, the cover may be electrically neutral (unpowered) and/or electrically insulated to protect surrounding tissue and treating personnel, as described above. Such covers should be capable of compressing the tissue in order to inhibit blood flow to and from the target region being treated. By inhibiting blood flow, energy losses can be minimized and temperature uniformity enhanced. The covers may be rigid plates, conformable surfaces, or the like, and will typically be clipped or otherwise removably or positionably attached to a primary treatment probe. In addition to being electrically insulated, the cover will preferably also be thermally insulating to protect adjacent tissue structures from thermal damage and further to inhibit heat losses from the tissue which is being treated. While in some instances the cover may be discontinuous, i.e., perforated or having other openings or apertures, it will usually be desirable to utilize a cover having a continuous surface which can inhibit the loss of steam from the tissue which is being treated. Containment of steam within the region being treated further enhances tissue heating. Preferably, the compressive force between a deployed electrode array on the primary treatment probe and the cover on the tissue surface will be in the range from 0.5 psi to 1.5 psi, preferably 0.8 psi to 1.2 psi.

A method according to the present invention for treating a target region beneath a tissue surface, such as a tumor site closely beneath the surface of an organ, comprises deploying a first array of electrodes in the tissue at or near the target region, preferably being distal to the site. A second electrode is deployed on the tissue surface over the target region, and an electrical current, typically radio or other high frequency current, is then applied to the tissues through the electrodes. The current may be applied in a monopolar fashion, i.e. with the first array of electrodes and the second electrode being simultaneously and/or successively connected to one pole of a power source and a dispersive or passive electrode disposed on the patient's outer skin attached to the other pole. Alternatively, the first array of electrodes and the second electrode may be powered in a bipolar fashion by attaching them to opposite poles of the power supply.

The first array of electrodes is preferably deployed by positioning a probe so that a portion of the probe lies near the target region in the tissue to be treated. A plurality of at least three array electrodes is then advanced radially outwardly from the probe to define the first electrode array. The probe may be advanced directly into tissue, e.g. using a sharpened distal tip on the probe itself, or may be introduced together with a stylet which is then removed in order to permit introduction of the electrodes through the probe. Conveniently, the probe for deploying the electrode array may be constructed similarly or identically to a LeVeen™ Needle Electrode as described in WO 96/29946. With such LeVeen™ Needle Electrodes, the electrodes advance initially in the forward direction and then evert (i.e. follow an arcuate path from the tip of the probe) outwardly as they are further advanced into the tissue. The electrodes will preferably deploy outwardly to span a radius of from 0.5 cm to 3 cm when the individual electrode elements are fully extended. The array electrodes may be deployed at a depth below the tissue surface in the range from 2 cm to 10 cm, preferably from 3 cm to 5 cm, (based on the position of the probe tip), with all individual electrode elements preferably lying completely within tissue.

The second electrode may comprise a plate or other electrode structure which is engaged directly against the tissue surface. The plate or other structure will usually have an active electrode area in the range from 3 $cm^2$ to 15 $cm^2$, preferably from 5 $cm^2$ to 10 $cm^2$. The second electrode may further comprise a plurality of tissue-penetrating electrode elements which penetrate into the tissue when the second electrode is engaged against the tissue surface. The tissue-penetrating electrode elements will usually be distributed over an area as set forth above for the plate electrode, and will preferably be capable of being penetrated to a depth below the tissue surface in the range from 3 mm to 10 mm, preferably from 4 mm to 6 mm. The tissue-penetrating elements will usually be parallel to each other, more usually being normal or perpendicular to a planar support plate, and are preferably pins having a diameter in the range from 1 mm to 3 mm, preferably from 1.5 mm to 2 mm, and a length sufficient to provide the tissue penetration depths set forth above. Optionally, the second electrode can be attached to the probe after the first electrode array has been advanced and deployed beneath the tissue. By attaching the second electrode to the probe, the entire system can be immobilized while the target region is being treated.

The active electrode area of both the first electrode array and second electrode will be the surface area of the electrode structure which is expected to come into contact with tissue in order to transfer electrical current. The total active electrode area of the first array of electrodes will typically be in the range from 1 $cm^2$ to 5 $cm^2$, preferably from 2 $cm^2$ to 4 $cm^2$. The area for the exemplary LeVeen™ Needle electrode is about 3 $cm^2$. The active electrode area for the second electrode will be in the ranges generally set forth above. In the case of second electrodes having pins projecting from the surface of a plate, the active electrode area may be defined by the pins, the plate surface, or a combination of both. It will be appreciated that portions of the plate and/or the pins may be covered with electrical and thermal insulation to achieve desired tissue treatment patterns. Portions of the first array of electrodes may also be insulated in order to change the electrical transfer characteristics. For monopolar operation, there is generally no requirement that the electrode areas of the first electrode array and the second electrode be the same. In the case of bipolar operation, however, it will generally be desirable that the total electrode areas of both the first array of electrodes and the second electrode be generally the same, usually differing by no more than 20%, preferably differing by no more than 10%.

In an alternative method according to the present invention, control of heat-mediated necrosis of a target region in tissue may be improved by inhibiting blood flow into the target region prior to the heat treatment. Large volume ablation and necrosis of highly vascularized tissue, such as liver tissue, can be difficult because of thermal transport from the region due to local blood flow. That is, blood flow through the tissue carries heat away. Moreover, because the degree of vascularization in any particular region is unpredictable, the total amount of heat which must be delivered in order to effectively necrose the tissue is difficult to predict. Heat-mediated tissue necrosis may thus be improved by inhibiting blood flow into the treatment region prior to heating. In some instances, it may be possible to tie off or clamp blood vessels(s) going into the region. Other known techniques for inhibiting blood flow and consequent heat loss include lowering blood pressure to reduce blood flow in all regions of the body. For thermal treatment according to the present invention, however, it will be preferred to first necrose tissue at or near a distal periphery of the target region so that the vasculature is at least partly destroyed in order to reduce the blood flow into the and/or the target region. Most preferably, this two-step method will be achieved using the first array of electrodes and second electrode as generally described above, where the second electrode is first energized to necrose tissue at or near the periphery of the target region. While this approach is presently preferred, it will be appreciated that other heating modalities could also be employed, such as microwave heating, dispersed laser energy heating, electrical resistance heating, introduction of heated fluids, and the like.

In a still separate aspect of the methods of the present invention, deployment of the first electrode array and second electrode or other cover in a manner such that tissue is compressed therebetween will (after deployment) also inhibit blood flow into and from the target region between the electrodes. Thus, the step of inhibiting blood flow may be achieved as simply as compressing the tissue in order to reduce blood flow through the target region between the electrodes. The compressive forces may be applied by any structure deployed over or otherwise adjacent to the tissue region being treated, usually being positioned directly over the target region in the organ being treated. Typically, the primary electrode which is deployed within the tissue will act as an anchor and the cover or other structure will be secured to a probe or shaft which is part of the electrode. The cover and electrode can then be drawn together and secured in place to compress all or a portion of the tissue volume being treated. In this way, blood flow into and out of the region may be significantly decreased. Optionally, such compression is achieved using treatment electrodes which are also used for introducing a frequency or other electrical current into the treatment region to effect the heating.

The presence of a cover or second electrode structure can also be relied on to facilitate deployment of the first electrode array. As discussed above, the first electrode array is preferably deployed by positioning a probe so that a portion of the probe lies near the target region in the tissue to be treated. The cover or second electrode structure may be utilized to help initially initial the probe. After determining a desired treatment depth, e.g., based on computed tomography (CT), the position of the cover or second electrode structure on the probe may be fixed so that the distal end of the probe will penetrate tissue to the desired depth when the cover or second electrode structure engages the upper skin or tissue surface. Thus, the cover or second electrode structure may be used as a positioning "stop" in the initial deployment of the probe and first electrode array. After deployment of the first electrode array, the cover or second electrode array can optionally be moved toward the first array and the tissue compressed between the two as also described above.

While the preferred compression apparatus will use an anchor electrode and an external compression structure (either electrically active or neutral), it will also be possible to use a pair of spaced-apart structures penetrated into tissue for compressing the tissue therebetween. Either or both of the spaced-apart structures may be electrically active, e.g., acting as energy-applying electrodes for performing the methods of the present invention. Alternatively, the spaced-apart structures may both be electrically unpowered so that they compress tissue only and other electrode(s) are used for directing electrical energy to tissue.

Systems according to the present invention for treating a target region in tissue beneath the tissue surface comprise a probe having a distal end adapted to be positioned beneath the tissue surface and within or just proximal to a target region in the tissue. A plurality of electrodes are deployable from the distal end of the probe to span a region of tissue proximate the target region, usually just distal to the site. The system further includes a cover, such as a surface electrode, adapted to span an area of the tissue surface over the target region. Other exemplary covers include rigid plates, typically in the form of a disc having a generally circular or oval periphery, conformable surfaces, such as foam layers, polymer discs, deployable electrode structures having tissue-contacting surfaces, or any other mechanical structures which can be deployed over or contacted against tissue to provide a relatively uniform compressive force against the tissue. Preferably, a surface electrode comprises a support having an electrode face and an insulated face opposite to the electrode face. In the first embodiment, the electrode face may be generally flat and have an area in the ranges set forth above. Alternatively, the surface electrode may comprise a plurality of tissue-penetrating elements on the face of a plate or other support structure, typically from four tissue-penetrating elements to sixteen tissue-penetrating elements, more preferably from six tissue-penetrating elements to nine tissue-penetrating elements. Optionally, the tissue-penetrating elements may be arranged in a circular, grid, concentric ring, serpentine, zig-zag, staggered, or other pattern on the electrode face, further optionally with additional electrodes interior to the peripheral electrodes. The tissue-penetrating elements preferably comprise pins having the sizes described above.

The surface electrode may optionally be connected to the probe using a connector. Usually, the connector will attach the surface electrode in a generally transverse orientation relative to the axis of the probe. Optionally, the connector can be flexible or in the form of a swivel or "universal joint" which permits the surface electrode to align itself with the tissue surface even when the probe is entering at an angle relative to the tissue surface which is not perpendicular. Other suitable connectors include clips, pinch clamps, threaded connectors, hook and loop fasteners (such as VELCRO™ brand fasteners), and the like. The connectors should allow the surface electrode or other cover to be selectively attached at various points along the length of the probe. Optionally, the probe can be marked with indicia indicating the depth of penetration, i.e., length between the distal tip of the probe and the particular point on the probe where the surface electrode or other cover may be attached. The ability to connect the surface electrode or other cover to the probe prior to deployment of the first electrode array is useful in helping to position the probe at a desired treatment depth, as described elsewhere herein.

The surface electrode and the probe may be electrically isolated from each other or may be electrically coupled to a common pole for monopolar operation. For simultaneous monopolar operation, the surface electrode (and any tissue-penetrating elements thereon) will be electrically coupled to the deployable electrode array on the probe so that all of the electrodes in the system can be connected to one pole of an electrode surgical power supply. Alternatively, the array electrodes on the probe may be electrically isolated from the second electrode and any tissue-penetrating elements thereon. When electrically isolated, the electrode array and surface electrode can be driven separately (one at a time) in a monopolar fashion or simultaneously in a bipolar fashion, i.e. each connected to the opposite pole of an electrosurgical power supply.

The probe will usually comprise a cannula having a proximal end, a distal end, and a lumen extending to at least the distal end. The deployable electrodes are resilient and disposed within the cannula lumen to reciprocate between a proximally retracted position where all electrodes are radially constrained within the lumen and the distally extended where all electrodes deploy radially outwardly. Usually, the electrodes will have a shape memory which will deflect the electrodes radially outwardly as they extend from the cannula. The most preferred configuration for the deployable electrodes is arcuate so that they assume an outwardly everted configuration as they are extended from the cannula. Usually, the array electrodes are connected to a rod structure which is reciprocatably received in the cannula lumen. Optionally, a stylet may be provided as part of the system for placement in the cannula so that a sharpened tip of the cannula extends beyond the distal tip of the cannula. The cannula and stylet may then be introduced to the target region through tissue, after which the stylet is removed leaving the lumen for receiving the electrode array. Usually, the cannula will have a length in the range from 5 cm to 30 cm, preferably from 12 cm to 25 cm, and an outer diameter in the range from 1 mm to 5 mm, usually from 1.5 mm to 2 mm. The electrode array will deploy outwardly to a radius in the range from 0.5 cm to 3 cm, preferably from 1 cm to 2 cm when fully extended. The electrode array will include at least 5 electrodes, preferably including at least 8 electrodes, and often including 10 or more electrodes.

Kits according to the present invention will comprise at least a second electrode, together with instructions for use for deploying an electrode array in tissue and engaging the second electrode on a tissue surface above the deployed electrode array for treating a tumor or other disease condition at or near the tissue surface. Usually, the second electrode (optionally together with a first electrode array) will be packaged in a conventional medical device package, such as a tray, box, tube, pouch, or the like. The instructions for use may be provided on a separate sheet of paper or may be printed in whole or in part on a portion of the packaging.

DESCRIPTION OF THE SPECIFIC EMBODIMENTS

Figure 1:
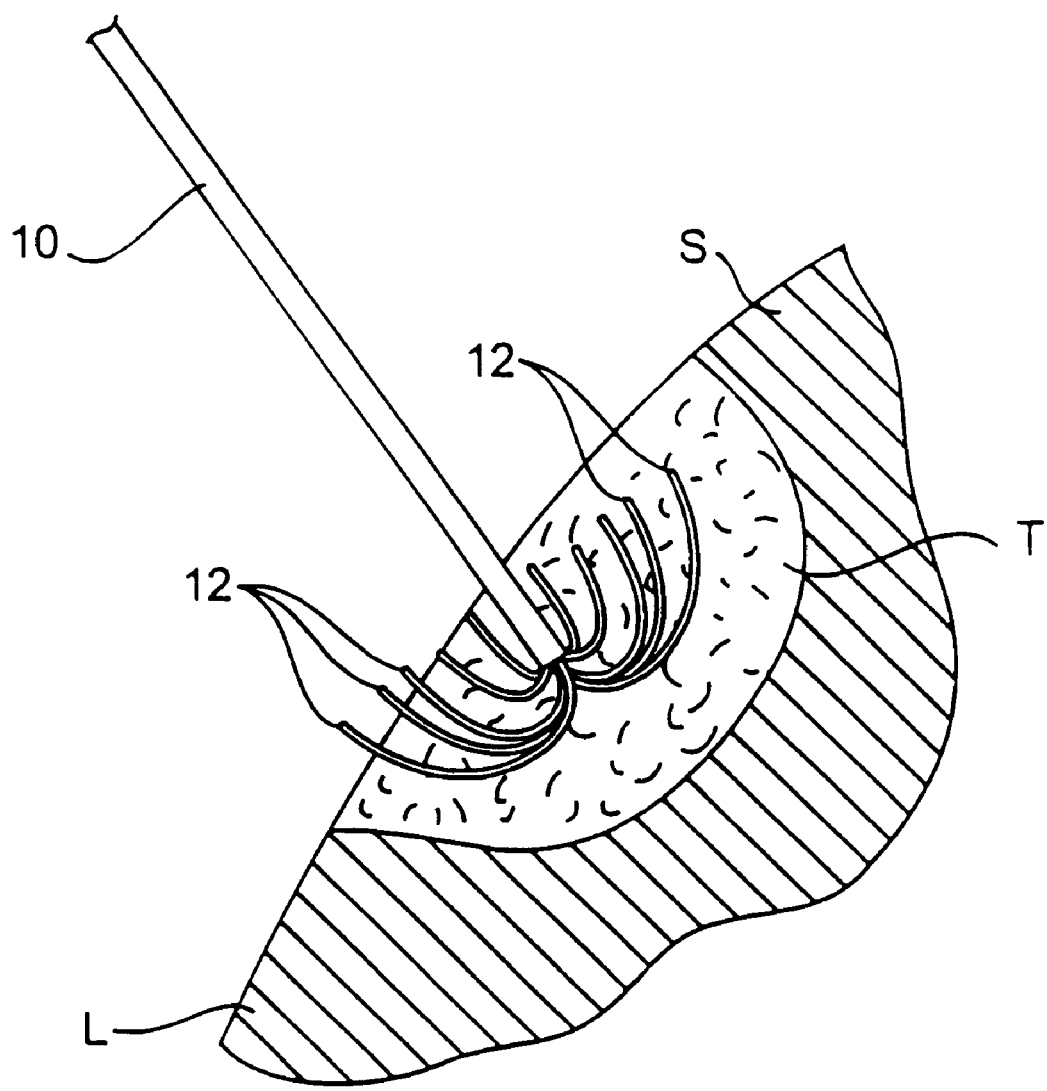
FIG. 1 illustrates deployment of the prior art LeVeen™ Needle Electrode array for treatment of a tumor region near the surface of a liver, with several of the electrode tips being shown exposed.

Systems according to the present invention are designed to position electrode elements and assemblies within and over a treatment region within solid tissue of a patient. The treatment region may be located anywhere in the body where hyperthermic exposure may be beneficial. Most commonly, the treatment region will comprise a solid tumor within an organ of the body, such as the liver, kidney, pancreas, breast, prostate (not accessed via the urethra), and the like. The volume to be treated will depend on the size of the tumor or other lesion, typically having a total volume from 1 cm$^3$ to 150 cm$^3$, usually from 1 cm$^3$ to 50 cm$^3$, and often from 2 cm$^3$ to 35 cm$^3$. The peripheral dimensions of the treatment region may be regular, e.g. spherical or ellipsoidal, but will more usually be irregular. The treatment region may be identified using conventional imaging techniques capable of elucidating a target tissue, e.g. tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound which can be employed to monitor the size and location of the tumor or other lesion being treated, either intraoperatively or externally.

Of particular interest to the present invention, tumors and other treatment regions which lie at or near the surface of a body organ or other tissue mass may be effectively treated by deploying a first array of electrodes in the tissue at or within the target region, typically being positioned at the posterior periphery of the region to be treated, and deploying a cover or a second electrode on the tissue surface over the target region. The cover can be any structure which can be secured to the first array of electrodes in order to cover and/or compress tissue between the surface and the region in which the first electrode is being deployed. In a first instance, the cover will not be used for imparting electrical energy, usually being at least partly formed from or covered by an electrically and/or thermally insulating material. In such instances, the cover will only act to isolate and/or compress the tissue. In other cases, the cover will be in the form of a second electrode as described below. The second electrode may be a generally planar electrode but will preferably comprise a plurality of tissue-penetrating electrode elements which can penetrate through the tissue surface to provide effective electrical coupling and current distribution to the tissue being treated. By then applying electrical current, usually radio or other high frequency current, to the tissue through the first array of electrodes and the second electrode, sequentially or simultaneously, the tissue can be effectively treated both at or near the surface as well as at lower depths within the tissue region.

Systems according to the present invention will usually comprise of a probe having a distal end adapted to be positioned beneath the tissue surface at or near the target region or region. A plurality of tissue-penetrating electrodes, typically in the form of sharpened, small diameter metal elements are reciprocatably attached to the probe so that they penetrate into tissue as they are advanced from a target region within the target region, as described in more detail hereinafter. The primary requirement of such electrode elements is that they can be deployed in an array, preferably a three-dimensional array, emanating generally from a target region within the treatment region of the tissue. In the exemplary embodiment, the electrode elements are first introduced to the target region in a radially collapsed or other constrained configuration, and thereafter advanced into the tissue from a delivery cannula or other element in a divergent pattern to achieve the desired three-dimensional array. The electrode elements will diverge radially outwardly from the delivery cannula (located at the target region) in a uniform pattern, i.e. with the spacing between adjacent electrodes diverging in a substantially uniform and/or symmetric pattern. Preferably, pairs of adjacent electrodes will be spaced-apart from each other in similar or identical, repeated patterns and will usually be symmetrically positioned about an axis of the delivery element. The electrode elements may extend or project along generally straight lines from the target region, but will more usually be shaped to curve radially outwardly and optionally to evert proximally so that they face partially or fully in the proximal direction when fully deployed. It will be appreciated that a wide variety of particular patterns can be provided to uniformly cover the region to be treated.

The second electrode, also referred to herein as the surface electrode, is intended to provide electrical contact with a region of the tissue surface which is located generally over the target region with the tissue. When the tumor or other target region extends to the tissue surface, the second electrode will preferably be positioned to cover all or as much of the exposed tumor as possible. In its simplest form, the second electrode may be a generally flat or planar plate electrode, e.g. being a simple disc having an area within the ranges set forth previously. Preferably, however, the second electrode will comprise a plurality of tissue-penetrating electrode elements which project perpendicularly from the electrode plate or other support structure. The tissue-penetrating electrode elements will form part of the electrically conductive electrode structure, with the supporting plate or other structure being either active or inactive, i.e. the rest of the supporting structure may be insulated so that it is not electrically active when in contact with tissue. In almost all cases, the opposite face of the electrode structure, i.e. all portions of the electrode which are not intended to contact tissue, will be electrically and thermally insulated to prevent accidental tissue contact with electrically active and heated components of the electrode during performance of a procedure. The tissue-penetrating elements may be simple blunt pins, sharpened pins, or needles which project perpendicularly from the planar electrode support, usually having dimensions within the ranges set forth above. The number of tissue-penetrating elements on the second electrode will also be within the ranges set forth above. The electrically conductive components of the second electrode, including all those which come into contact with tissue, will usually be formed from or plated with an electrically conductive metal, such as stainless steel, gold, silver, brass, and the like.

The second electrode will preferably be attachable to the probe which deploys the first electrode array, usually being attached after the first electrode array is deployed. In the exemplary embodiment, the second electrode is a disc structure having a central aperture which can be selectively and slidably positioned over the probe shaft and locked into position. In such cases, the second electrode will be disposed in a generally transverse orientation when the electrode is locked on the probe. When the second electrode carries tissue-penetrating elements, those elements will usually be aligned in a parallel orientation with the axis of the probe. In some cases, however, it may be desirable to attach the second electrode so that it is capable of pivoting or otherwise adjusting its planar orientation relative to the axis of the probe. For example, the second electrode may be attached using a ball-and-socket or other universal joint which permits relatively free movement of the second electrode about the pivot point defined by the attachment to the probe. In the exemplary embodiments, if the tumor being treated approaches or reaches the surface of the tissue or organ, the second (surface) electrode may be placed onto the shaft of the probe after the first electrode array is deployed. Deployment of the first electrode array will anchor the distal end of the probe in tissue, permitting the second electrode to be firmly engaged against the tissue surface, preferably so that tissue between the deployed electrode array and the second electrode array and the second electrode will be slightly compressed. Such compression has at least two advantages. First, both electrodes are held firmly in place so that they are less likely to become dislodged. More importantly, compression of the tissue tends to inhibit blood flow into the treatment region rendering heating of the tissue more rapid and more controllable. When employing tissue-penetrating elements on the second electrode, it is desirable that they be fully inserted into the tissue. The depth of tissue penetration by the elements largely determines the depth of the surface lesion being created, i.e. the more fully the elements penetrate into tissue, the deeper the lesion will be.

Monopolar operation may be effected in two ways. Most commonly, the first electrode array and second electrode will be electrically isolated from each other and powered separately, preferably with the first electrode array being powered first in order to necrose tissue at a boundary of the target region and inhibit blood flow into the region. In other cases, however, if sufficient power is available, the first electrode array and second electrode may be driven simultaneously while attached to a common pole on an electrosurgical power supply. Although not essential, the first electrode array and second electrode may have similar available electrode areas, so that approximately the same heating will occur from both the electrodes simultaneously, but at half the power level which will be achieved using the same power level with only a single electrode.

For bipolar operation, the electrically conductive components of the second electrode will be electrically isolated from the electrically conductive components of the first electrode array. In that way, the second electrode and first electrode array can be attached to opposite poles of a radiofrequency or other power supply in order to effect bipolar current flow between the deployed electrode components. Preferably, the available surface areas of the first electrode array and the second electrode will be approximately equal so that heating (energy transfer into unit volumes of adjacent tissue) occurs at approximately the same rate from both electrode structures. If the areas differ significantly from each other, the current flux from the smaller electrode will be denser, which can cause premature desiccation at one electrode before the entire target tissue region has been effectively heated. Premature desiccation limits the ability of the electrode to pass current through the tissue, rendering further treatment difficult.

It will be appreciated that in monopolar operation, a passive or dispersive "electrode" must also be provided to complete the return path for the circuit being created. Such electrodes, which will usually be attached externally to the patient's skin, will have a much larger area, typically about 130 $cm^2$ for an adult, so that current flux is sufficiently low to avoid significant heating and other biological effects. It may also be possible to provide such a dispersive return electrode directly on a portion of a sheath, core element, or other portion of the system of the present invention (generally, when the return electrode is on the same sheath or core, the device may still be referred to as bipolar).

The RF power supply may be a conventional general purpose electrosurgical power supply operating at a frequency in the range from 300 kHz to 1.2 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for the methods of the present invention. Thus, such power supplies will usually be operated at the lower ends of their voltage and power capabilities. More suitable power supplies will be capable of supplying an ablation current at a relatively low voltage, typically below 150 V (peak-to-peak), usually being from 50 V to 100 V. Such low voltage operation permits use of a power supply that will significantly and passively reduce output in response to impedance changes in the target tissue. The power will usually be from 50 W to 200 W, usually having a sine wave form, but other wave forms would also be acceptable. Power supplies capable of operating within these ranges are available from commercial vendors, such as Radionics and RadioTherapeutics Corporation. A preferred power supply is model RF-2000, available from RadioTherapeutics Corporation, Mountain View, Calif., assignee of the present application.

The probe which contains the deployable electrode elements will usually be contained by or within an elongate member, typically a rigid or semi-rigid, metal or plastic cannula. In some cases, the cannula will have a sharpened tip, e.g. be in the form of a needle, to facilitate introduction to the tissue target region. In such cases, it is desirable that the cannula or needle be sufficiently rigid, i.e. have sufficient column strength, so that it can be accurately advanced through tissue. In other cases, the cannula may be introduced using an internal stylet which is subsequently exchanged for the electrode array. In the latter case, the cannula can be relatively flexible since the initial column strength will be provided by the stylet. The cannula serves to constrain the individual electrode elements in a radially collapsed configuration to facilitate their introduction to the tissue target region. The electrode elements can then be deployed to their desired configuration, usually a three-dimensional configuration, by extending distal ends of the electrode elements from the distal end of the cannula into the tissue. In the preferred case of the tubular cannula, this can be accomplished simply by advancing the distal ends of the electrode elements distally from the tube so that they emerge and deflect (usually as a result of their own spring or shape memory) in a radially outward pattern. Alternatively, some deflection element or mechanism could be provided on the elongate member to deflect members with or without shape memory in a desired three-dimensional pattern.

Referring to FIGS. 2–5, an exemplary electrode deployment system 20 constructed in accordance with the principles of the present invention. The system 20 comprises a probe 22 and a surface electrode 24. The probe 22 will be generally as described above, and will preferably be a LeVeen™ Needle Electrode of the type which is available from RadioTherapeutics Corp., Mountain View, Calif., assignee of the present application. The probe 22 comprises a handle 26 and a cannula 28, where the cannula has a sharpened distal tip 30 which may be directly introduced through tissue to a target region. As best observed in FIG. 3, a plurality of everting electrodes 32 may be deployed from the tip 30 by advancing a button 34 on the handle. The everting electrodes 32 are electrically coupled to a connector 40 (FIG. 2) at the proximal end of the handle 22 through a shaft 42 which is used to deploy the electrodes. The outer surface of the cannula 28 will be insulated so that current flows only through the everted electrodes 32 and the surface electrode 24.

Figure 2:
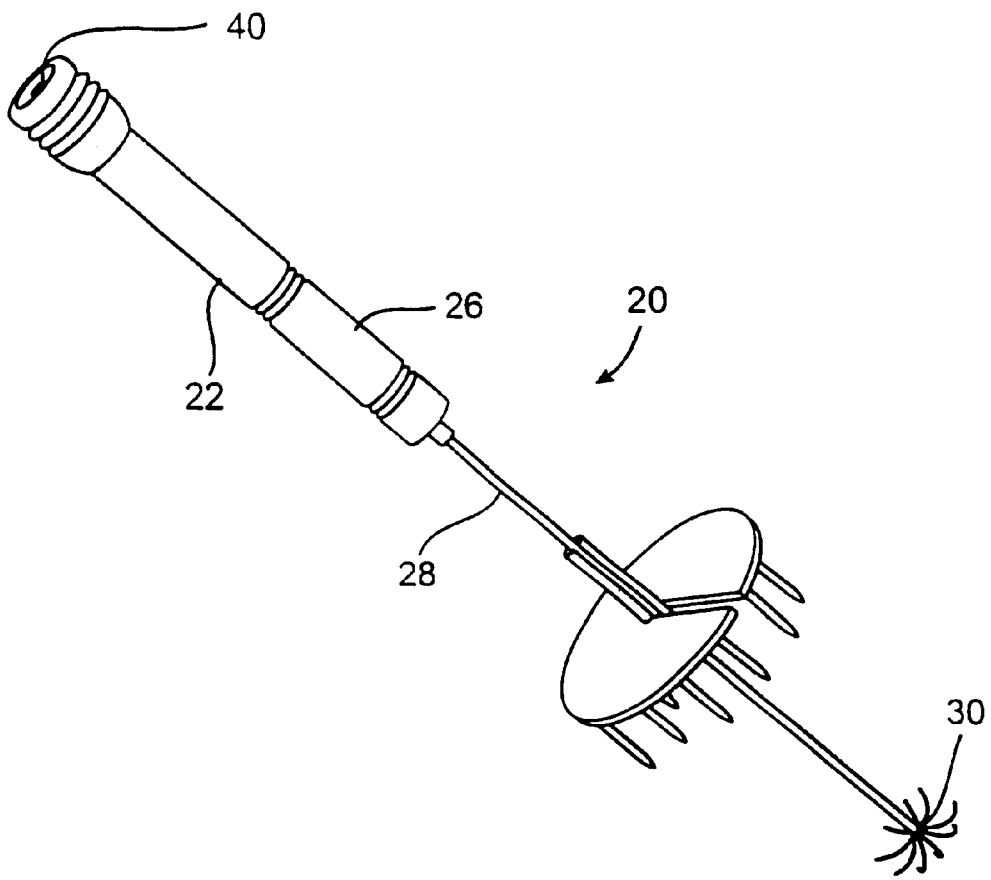
FIG. 2 illustrates and improved system according to the present invention comprising deployable electrode array, such as the LeVeen™ Needle Electrode, in combination with a surface electrode assembly.
Figure 2A:
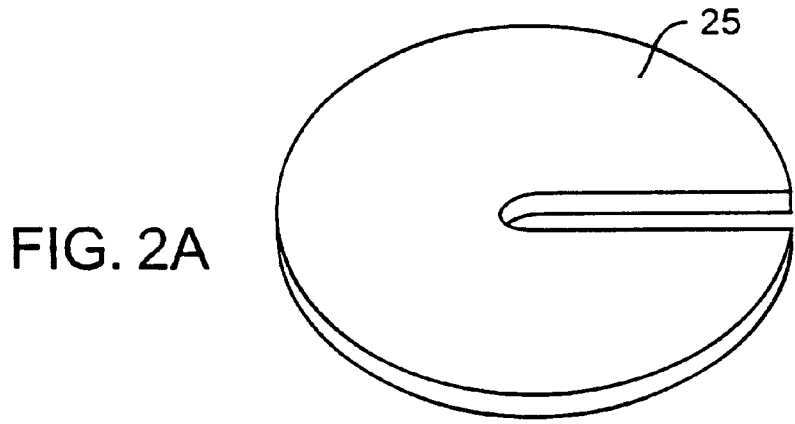
FIG. 2A illustrates a cover structure which can be used in place of the surface electrode assembly illustrated in FIG. 2.
Figure 3:
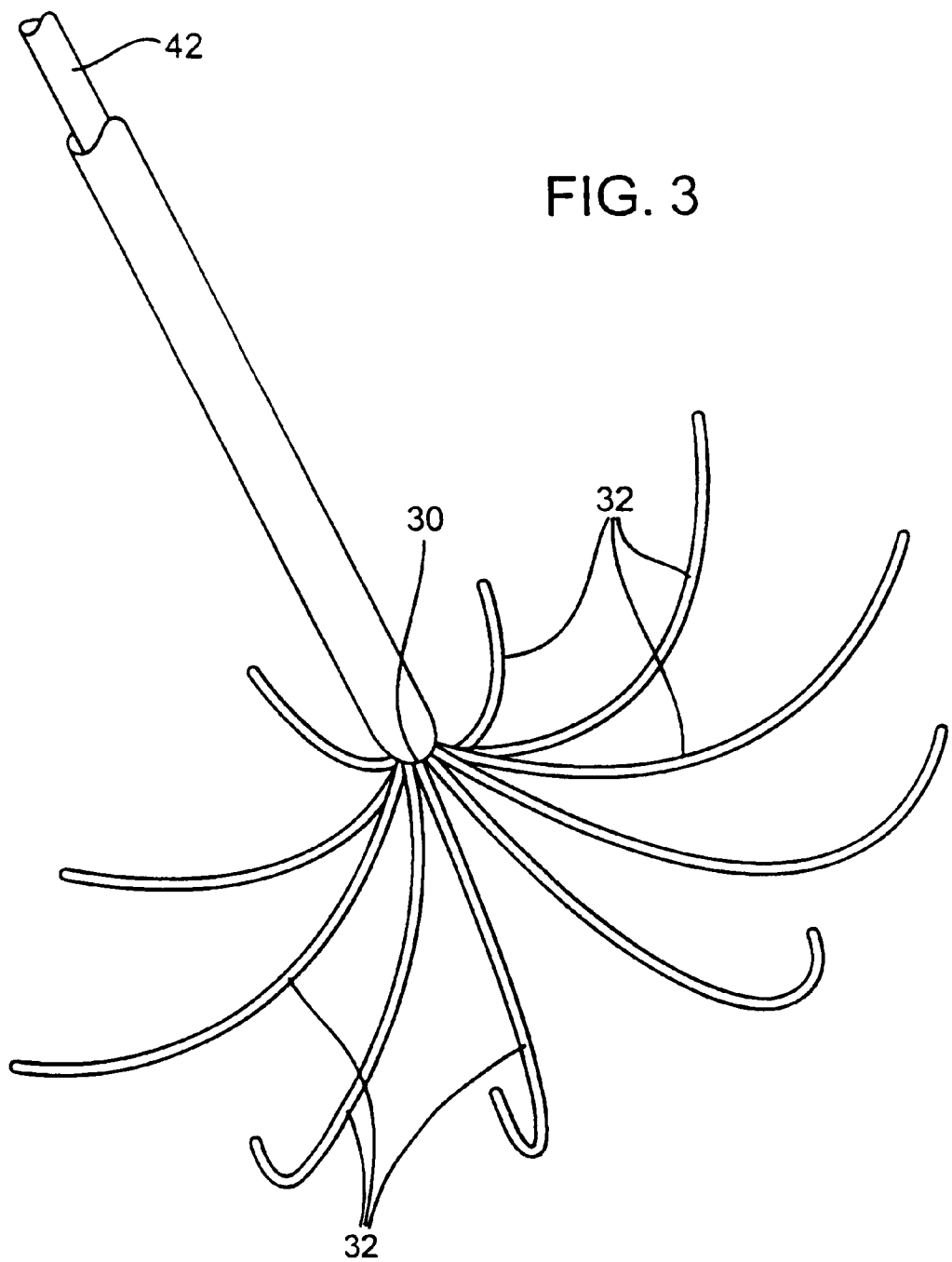
FIG. 3 is a detailed illustration of the distal end of the electrode array of FIG. 2, shown with the electrode array fully deployed.

As alternative to the second or surface electrode 24, a cover 25 may be used, as illustrated in FIG. 2A. The cover is not configured to act as an electrode and will usually be free from tissue-penetrating components. The cover will usually be disc-shaped and will generally have the dimensions of the electrode array 24. Unlike electrode array 24, however, the cover will not be intended for use as an electrode. Usually, at least a portion of the cover will be electrically and/or thermally insulating, i.e., formed from an electrically and/or thermally insulating material or covered by an insulator. Preferably, the cover will be both electrically and thermally insulating. Conveniently, the entire disc may be formed from a polymer, ceramic, or other material having a high electrical impedance to help isolate the region being treated and prevent accidental contact with the electrodes of array 30 deployed beneath the tissue surface. Usually, a clip or other fastening structure (not shown) will be provided on the cover 25 to permit selective mounting, positioning, and removal on to the shaft 28 of the system 20. A variety of suitable connectors have been described elsewhere herein.

Figure 4:
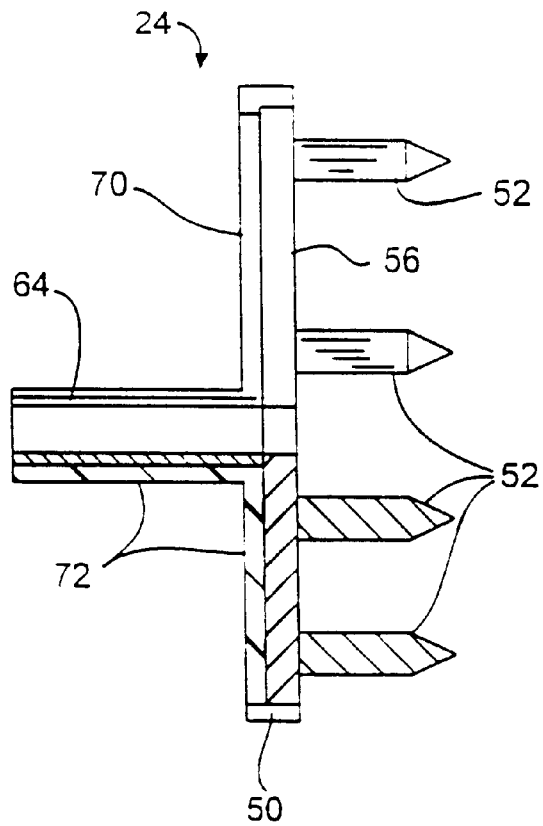
FIG. 4 is a side, cross-sectional view of the surface electrode that the system of FIG. 2.
Figure 5:
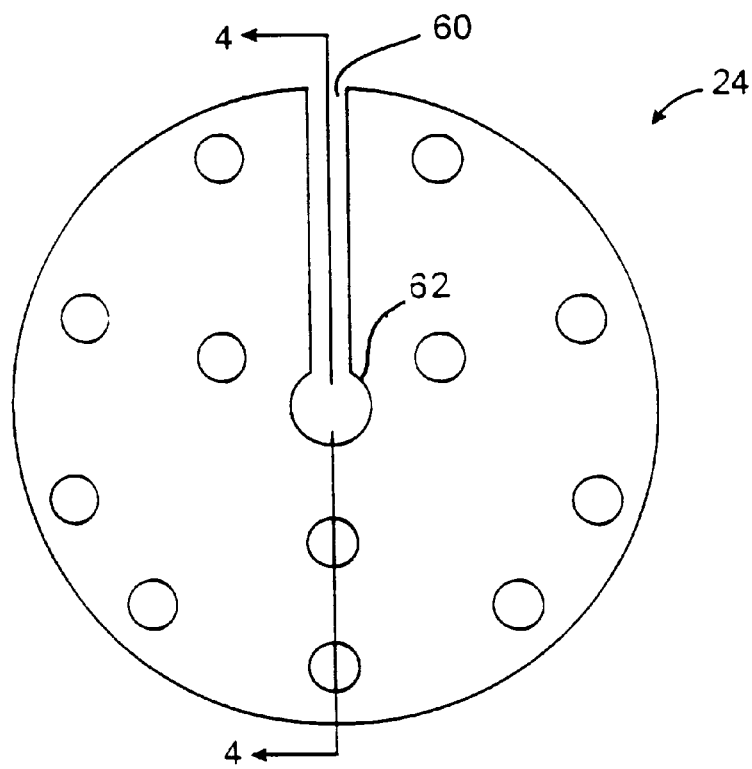
FIG. 5 is a bottom view of the surface electrode of the system of FIG. 2.

As best observed in FIGS. 4 and 5, the surface electrode 24 comprises an electrically conductive plate 50 having a plurality of tissue-penetrating pin electrodes 52 projecting forwardly from face 56 thereof. Preferably, the pin electrodes 52 will project in a generally perpendicular direction from the planar face 56. Usually, but not necessarily, face 56 will be covered with an insulating layer so that electrical contact is made through only the pins 52. In some cases, however, it may be desirable to leave the face 56 uninsulated so that electrical contact can be made through the face as well. A slot 60 is formed in the plate 50 so that the surface electrode 24 may be mounted onto the cannula 28 as seen in FIG. 2. An enlarged central aperture 62 may be provided for locking on to the cannula. Alternative locking mechanisms may also be provided, such as compression locks, latches, and the like (not illustrated) which permit axial movement of the surface electrode 24 along the length of cannula 28 and selective locking of the surface electrode at a desired position. Optionally, a collar 64 may be provided on the opposite face 70 of the plate to assist in holding and/or locking of the surface electrode 24 on the cannula 28. Preferably, electrical and thermal insulating layers 72 will be provided over all exposed portions of the surface electrode so that the chance of accidental contact between the surface electrode and other tissue structures near the treatment region is minimized. It will be appreciated that the surface electrode 24 may be attached at virtually any axial location along the cannula 28 so that the distance between the surface electrode and the distal tip (electrode deployment point) 30 of the probe 22 can be fully adjusted. Also, as described above, the connection between the cannula 28 and the surface electrode 24 can be made to freely pivot so that the electrode can adjust to different surface orientations of the tissue after the cannula 28 has been introduced into tissue.

Figure 6A:
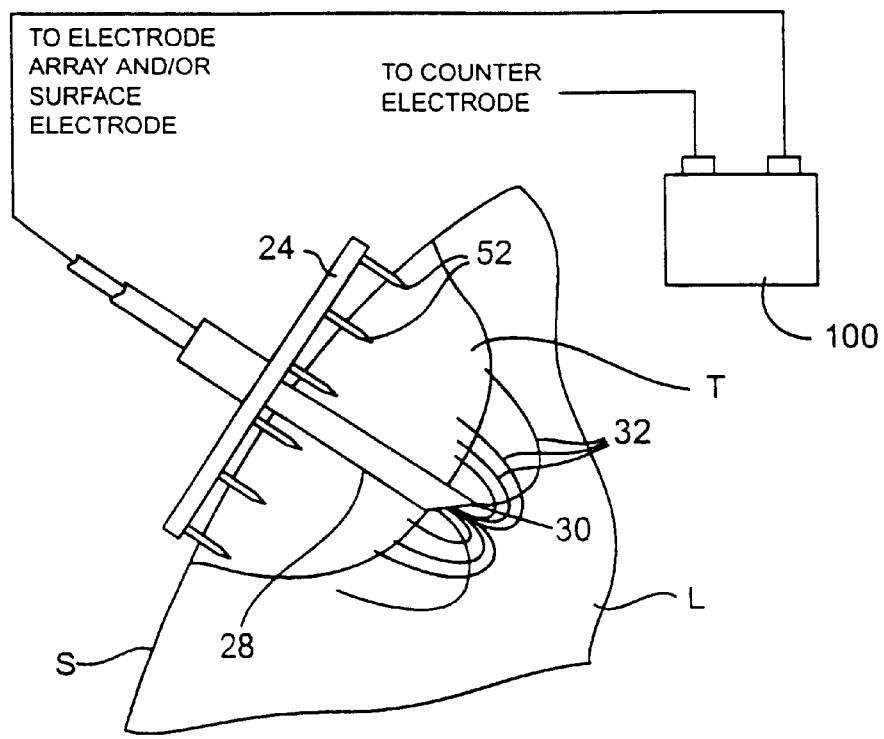
FIGS. 6A–6C illustrates the system of FIG. 2 being used for treatment of a surface tumor in a monopolar configuration.
Figure 6B:
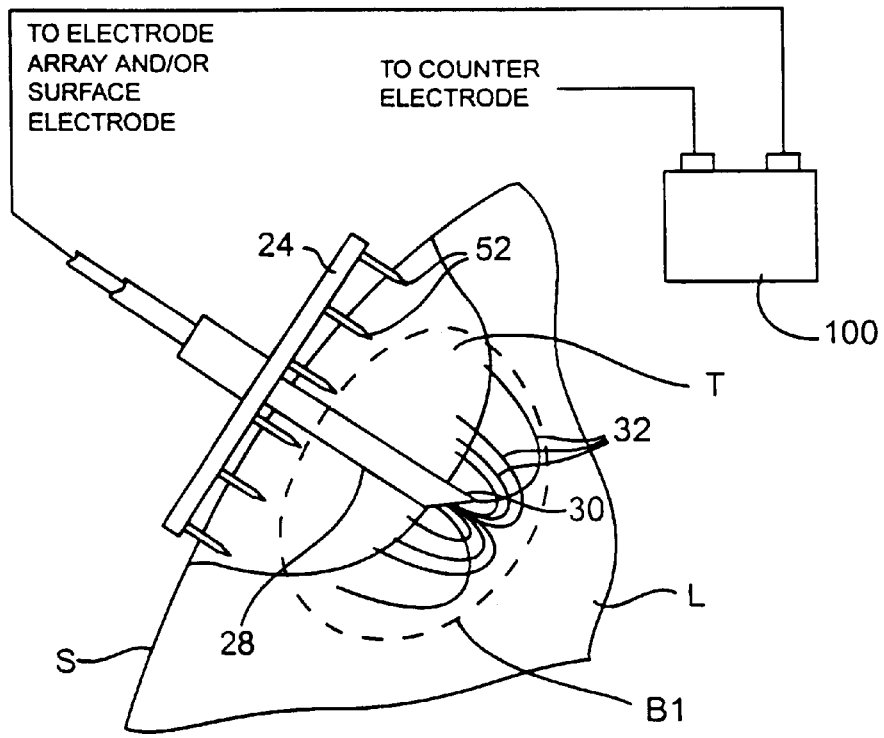
Figure 6C:
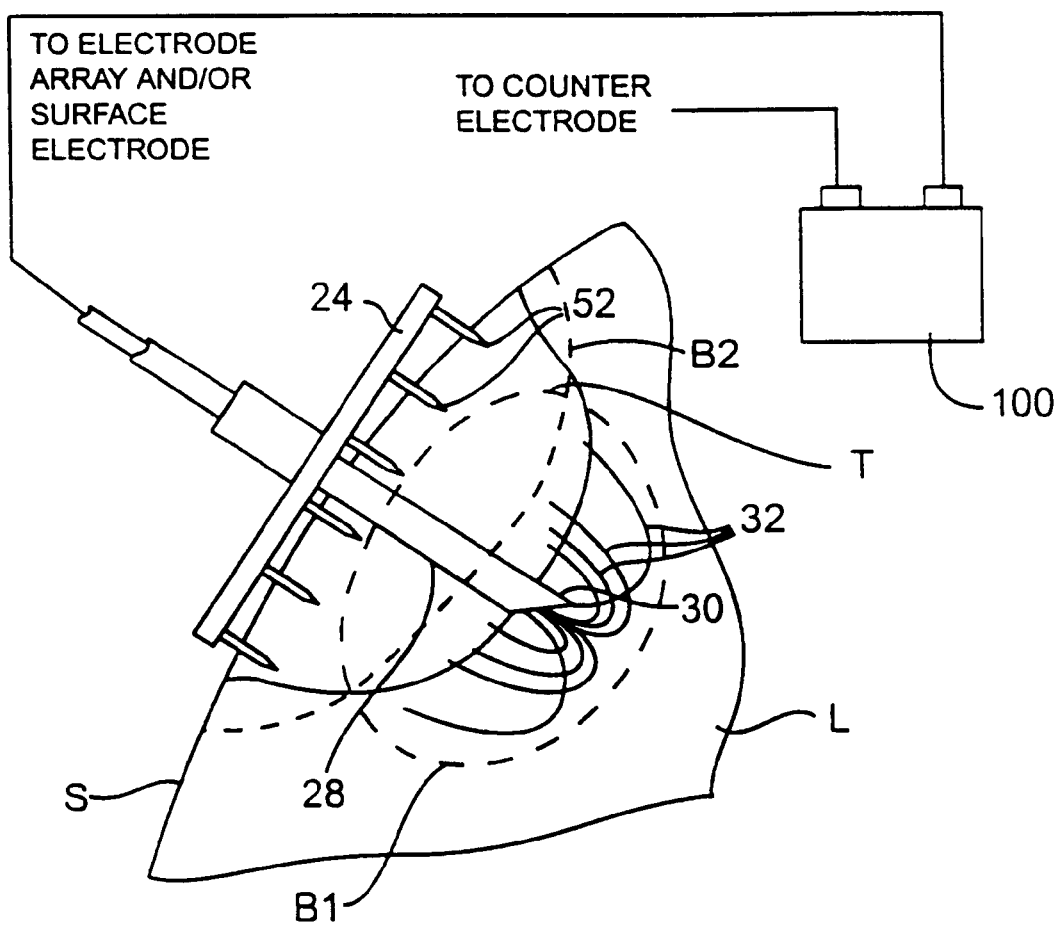

Referring now to FIGS. 6A–6C, monopolar operation of the electrode system 20 will be described. After imaging the tumor or other treatment region T in the liver L, the cannula 28 is introduced through the tissue surface F until the distal tip 30 advances to point generally at the posterior of the tumor region T. The electrodes 32 are then deployed by advancing them out of the distal tip 30, and the surface electrode 24 placed on to the cannula 28. The surface electrode 24 is then advanced toward the tissue surface S so that the electrode pins 52 advance into the tissue, and more particularly into the treatment region T, as illustrated in FIG. 6A. Current may then be applied in either of the two general modes described above. In a first mode (not illustrated) the surface electrode 24 and deployed electrodes are powered simultaneously to treat the entire target region T at once. In the illustrated and presently preferred mode, however, the deployed electrodes 32 are first energized to necrose a boundary region B1, as generally shown in FIG. 6B. Necrosis of the boundary region B1 will not only treat a significant portion of the tissue within the target region T, it will also at least partially inhibit blood flow into and from the target region to facilitate subsequent treatment with the surface electrode 24. After the first treatment step using deployed electrodes 32 is completed, the surface electrode 24 will be separately powered in order to treat a second boundary region B2 as shown in FIG. 6C. Preferably, these regions will at least partially overlap, and more preferably will completely overlap in order to fully necrose the treatment region T.

Figure 7:
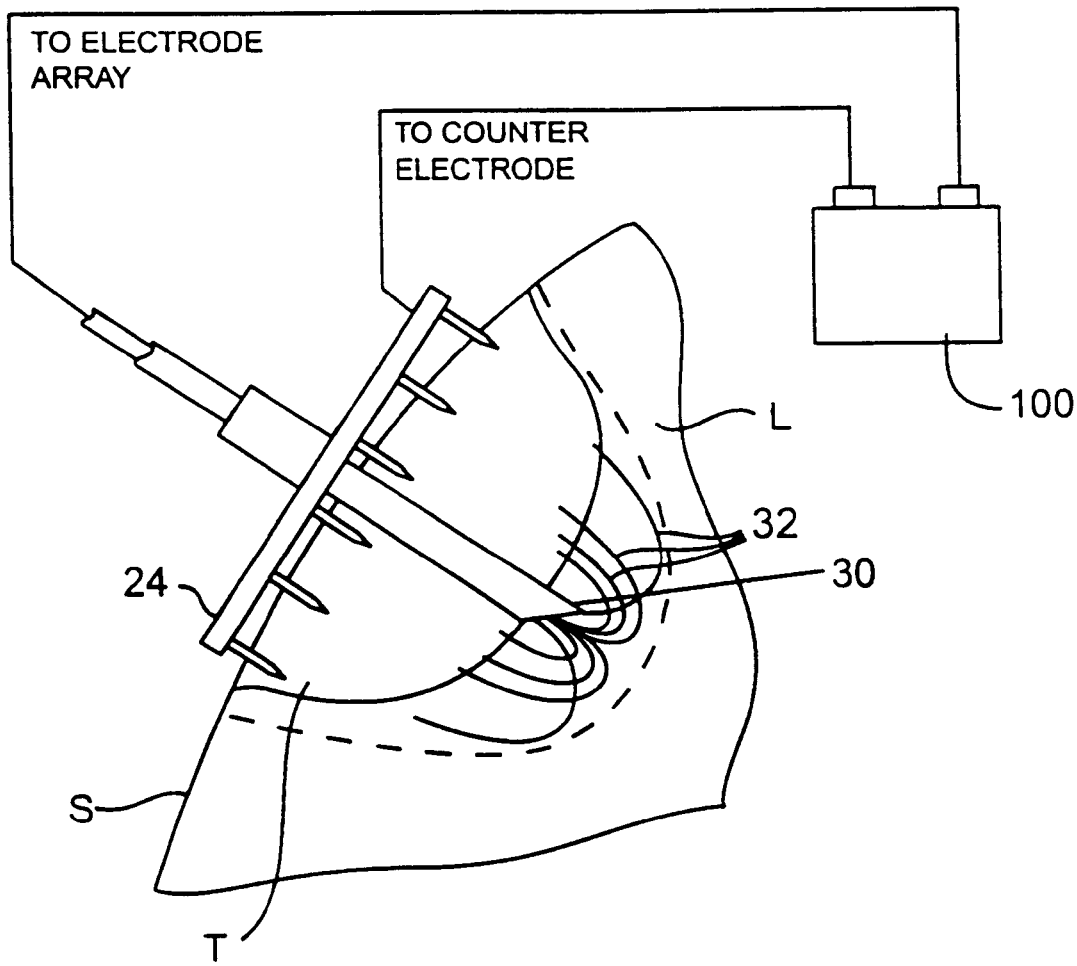
FIG. 7 illustrates the system of FIG. 2 connected for treatment of a surface tumor in a bipolar configuration.

Bipolar treatment according to the present invention is effected in manner very similar to that described for monopolar treatment. As shown in FIG. 7, electrodes 32 and surface electrode 24 are deployed on either side of the treatment region T. The electrodes 32 and 24 will, however, be electrically isolated from each other. A first pole of the power supply 100 is then coupled to the electrodes 32 of the interior electrode array while the second pole of the power supply is connected to the surface electrode 24. Radio or other high frequency energy can then be applied to the tissue in a bipolar fashion where current flows between the electrodes 32 and surface electrode 24, with the current flux being localized generally within the tumor or other treatment region T.

Figure 8:
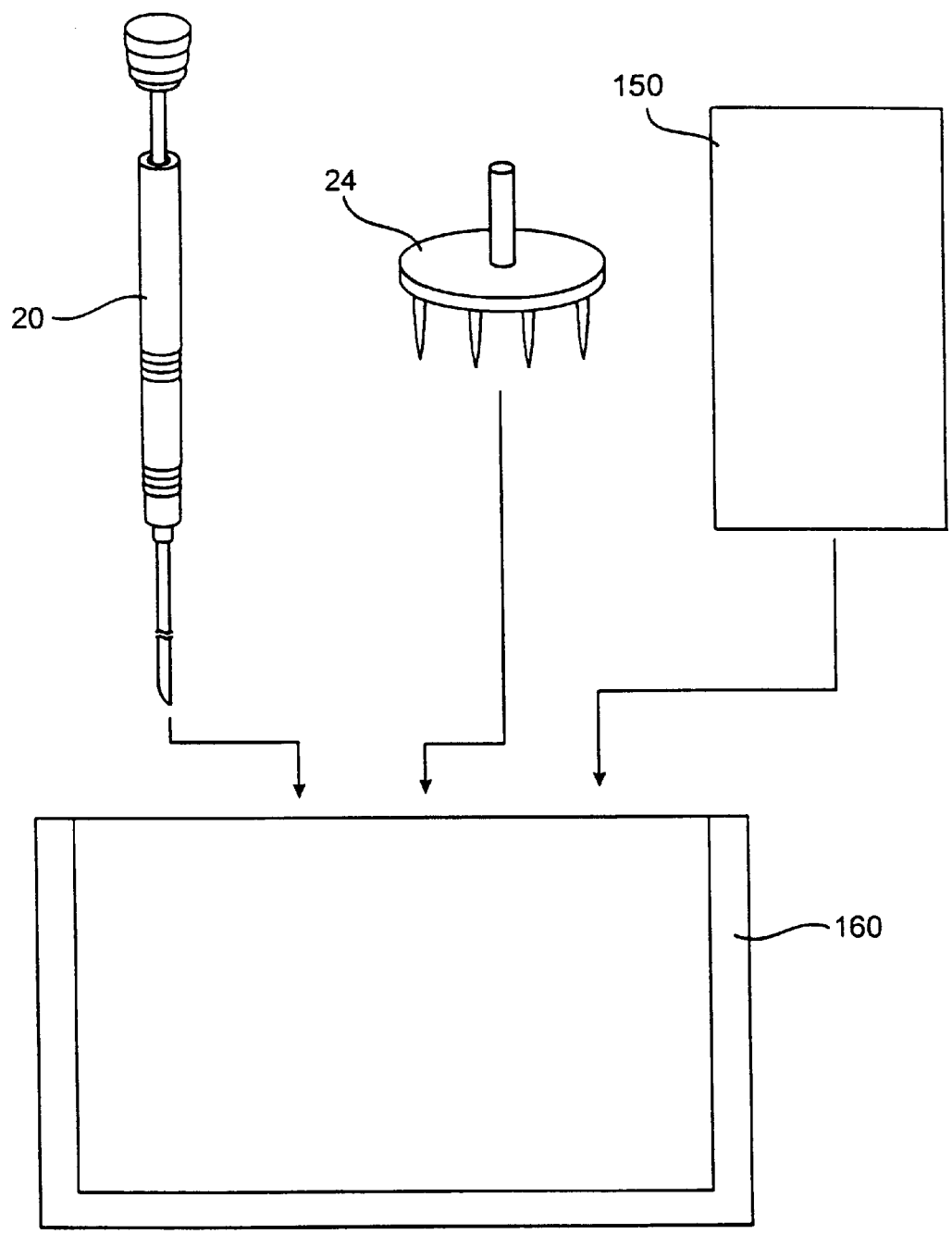
FIG. 8 illustrates a kit according to the present invention.

Referring now to FIG. 8, a kit according to the present invention will comprise at least a surface electrode 24, optionally a probe 20, and instructions for use IFU. The probe 20 and surface electrode 24 may be generally as described above, and the instructions for use will set forth a method for employing the probe 20 and the surface electrode 24 in accordance with any of the methods of the present invention described above. The instructions for use will generally be written on a package insert or other separate piece of paper 150, but may also be printed in whole or in part on the packing materials. Usually, all components of the kit will be packaged together in a conventional package 160, such as a pouch, tray, box, tube, or the like. Preferably, all system components will be sterilized within the package so that they are immediately ready for use in the sterile environment.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating a target region in tissue at or beneath a tissue surface, said method comprising:
    deploying a first array of electrodes in the tissue beneath the tissue surface at the target region;
    deploying a second electrode on the tissue surface over the target region; and
    applying electrical current to the tissue through the electrodes.

2. A method as in claim 1, wherein the high frequency current is applied successively from the electrodes in a monopolar mode.

3. A method as in claim 1, wherein high frequency current is applied with one pole attached to the array electrodes and another pole attached to the second electrode in a bipolar fashion.

4. A method as in claim 1, wherein deploying the second electrode comprises engaging a plate electrode against the tissue surface.

5. A method as in claim 4, wherein the plate electrode has an area in the range from 2 $cm^2$ to 10 $cm^2$.

6. A method as in claim 1, wherein deploying the second electrode comprises penetrating a plurality of tissue-penetrating electrode elements through the tissue surface.

7. A method as in claim 6, wherein the plurality of tissue-penetrating electrode elements are penetrated over an area in the range from 2 $cm^2$ to 10 $cm^2$.

8. A method as in claim 7, wherein the electrode elements are penetrated to a depth in the range from 3 mm to 10 mm.

9. A method as in claim 1, wherein high frequency current is applied simultaneously through both the array electrodes and the second electrode attached to a common pole of a power supply in a monopolar mode.

10. A method as in claim 6, wherein the tissue-penetrating electrode elements are pins having a diameter in the range from 1 mm to 3 mm and a depth from the electrode face in the range from 3 mm to 10 mm.

11. A method for treating a target region in tissue at or beneath a tissue surface, said method comprising:
    deploying a first array of electrodes in the tissue beneath the tissue surface at the target region;
    deploying a cover over the tissue surface over the target region, wherein the cover is configured to electrically and thermally isolate the target region and first electrode array from external tissue structures adjacent to the target region; and
    applying electrical current to tissue in the target region through the first array of electrodes.

12. A method as in any of claims 1, 2, or 11, wherein deploying the first 2 array of electrodes comprises:
    positioning a probe so that a portion of the probe is near the target region in the tissue; and
    advancing a plurality of at least three array electrodes radially outwardly from the probe to define the first electrode array.

13. A method as in claim 12, wherein the probe is advanced directly into tissue with the array electrodes retracted within the probe.

14. A method as in claim 12, wherein a combination of probe and stylet is initially advanced into the tissue, and wherein the stylet is withdrawn from the probe prior to advancing the array electrodes through the probe.

15. A method as in claim 12, wherein advancing the array electrodes comprises advancing them forwardly from a distal end of the probe so that the electrodes evert outwardly as they are advanced into the tissue.

16. A method as in claim 12, wherein the array electrodes deploy outwardly to a radius from 0.5 cm to 3 cm when fully distally extended.

17. A method as in claim 12, further comprising removably attaching the second electrode to the probe after the array electrodes have been advanced.

18. A method as in any of claims 1, 2, or 3, wherein the first array electrodes are deployed at a depth below the tissue surface in the range from 2 cm to 10 cm.

19. A method for treating a target region in tissue at or beneath a tissue surface, said method comprising:

deploying a first array of electrodes in the tissue beneath the tissue surface at the target region;

deploying a cover over the tissue surface over the target region, wherein the first array and cover are drawn together to apply compression on tissue in the target region; and applying electrical current to tissue in the target region through the first array of electrodes.

20. A method as in claim 19, wherein the electrical current is applied first through the first array of electrodes to necrose tissue at or near a boundary of the target region to inhibit blood flow into the target region.

21. A method as in claim 19 or 11, wherein the cover comprises a rigid plate.

22. A method as in claim 19 or 11, wherein the cover comprises a conformable surface.

23. A method as in claim 19 or 11, wherein the cover is composed of an electrically non-conductive material.

24. A method as in claim 19 or 11, wherein the cover and first electrode array are drawn together with a force of at least 0.5 psi.

25. A method as in claim 19 or 11, wherein deploying the first electrode array comprises positioning a probe so that a portion of the probe lies near the target region and deploying the cover comprises securing the cover to the probe after the probe has been deployed.

26. A method for treating a target region in tissue at or beneath a tissue surface, said method comprising:

deploying a first array of electrodes in the tissue at the target region;

penetrating a plurality of tissue-penetrating electrodes comprising a second electrode array through the tissue surface;

applying electrical current to the tissue through the electrodes.

27. A method as in claim 26, wherein deploying the first array of electrodes comprises:

positioning a probe so that a portion of the probe is near the target region in the tissue; and advancing a plurality of at least three array electrodes radially outwardly from the probe to define the first electrode array.

28. A method as in claim 27, wherein the probe is advanced directly into tissue with the array electrodes retracted within the probe.

29. A method as in claim 27, wherein a combination of probe and stylet is initially advanced into the tissue, and wherein the stylet is withdrawn from the probe prior to advancing the array electrodes through the probe.

30. A method as in claim 27, wherein advancing the array electrodes comprises advancing them forwardly from a distal end of the probe so that the electrodes evert outwardly as they are advanced into the tissue.

31. A method as in claim 27, wherein the array electrodes deploy outwardly to a radius from 0.5 cm to 3 cm wherein fully distally extended.

32. A method as in claim 27, further comprising removably attaching the second electrode to the probe after the array electrodes have been advanced.

33. A method as in claim 26, wherein the first array electrodes are deployed at a depth below the tissue surface in the range from 2 cm to 10 cm.

34. A method as in claim 26, wherein penetrating the second electrode comprises engaging a plate electrode against the tissue surface.

35. A method as in claim 34, wherein the plate electrode has an area in the range from 2 $cm^2$ to 10 $cm^2$.

36. A method as in claim 26, wherein the plurality of tissue-penetrating electrode elements are penetrated over an area in the range from 2 $cm^2$ to 10 $cm^2$.

37. A method as in claim 26, wherein the electrode elements are penetrated to a depth in the range from 3 mm to 10 mm.

38. A method as in claim 26, wherein the tissue-penetrating electrode elements are pins having a diameter in the range from 1 mm to 3 mm and a depth from an electrode face in the range from 3 mm to 10 mm.

39. A method as in claim 26, wherein high frequency current is applied simultaneously through both the array electrodes and the second electrode attached to a common pole of a power supply in a monopolar mode.

40. A method as in claim 26, wherein high frequency current is applied with one pole attached to the array electrodes and another pole attached to the second electrode in a bipolar fashion.

41. A method as in claim 26, wherein the high frequency current is applied successively from the electrodes in a monopolar mode.

42. A method for treating a target region in tissue at or beneath a tissue surface, said method comprising:

positioning a probe so that a portion of the probe is near the target region in tissue;

advancing a plurality of at least three array electrodes radially outwardly from the probe to define a first electrode array;

deploying a second electrode on the tissue surface over the target region;

removably attaching the second electrode to the probe after the first array electrodes have been advanced; and applying electrical current to the tissue through the electrodes.

43. A method for treating a target region in tissue at or beneath a tissue surface, said method comprising:

positioning a probe so that a portion of the probe is near the target region in tissue;

advancing a plurality of at least three array electrodes radially outwardly from the probe to define a first electrode array;

deploying a cover over the tissue surface over the target region, wherein the first array and cover are drawn together to apply compression on tissue in the target region;

removably attaching the second electrode to the probe after the first array electrodes have been advanced; and applying electrical current to tissue in the target region through the first array of electrodes.

44. A method for treating a target region in tissue at or beneath a tissue surface, said method comprising:

positioning a probe so that a portion of the probe is near the target region in tissue;

advancing a plurality of at least three array electrodes radially outwardly from the probe to define a first electrode array;

deploying a cover over the tissue surface over the target region, wherein the cover is configured to electrically and thermally isolate the target region and first electrode array from external tissue structures adjacent to the target region;

removably attaching the second electrode to the probe after the first array electrodes have been advanced; and applying electrical current to tissue in the target region through the first array of electrodes.

45. A method as in any of claims 42, 43, and 44, wherein the probe is advanced directly into tissue with the array electrodes retracted within the probe.

46. A method as in any of claims 42, 43, and 44, wherein a combination of probe and stylet is initially advanced into the tissue, and wherein the stylet is withdrawn from the probe prior to advancing the array electrodes through the probe.

47. A method as in any of claims 42, 43, and 44, wherein advancing the array electrodes comprises advancing them forwardly from a distal end of the probe so that the electrodes evert outwardly as they are advanced into the tissue.

48. A method as in any of claims 42, 43, and 44, wherein the array electrodes deploy outwardly to a radius from 0.5 cm to 3 cm wherein fully distally extended.

49. A method as in any of claims 42, 43, and 44, wherein the first array electrodes are deployed at a depth below the tissue surface in the range from 2 cm to 10 cm.

50. A method as in claim 42, wherein deploying the second electrode comprises engaging a plate electrode against the tissue surface.

51. A method as in claim 42, wherein the plate electrode has an area in the range from 2 $cm^2$ to 10 $cm^2$.

52. A method as in claim 42, wherein deploying the second electrode comprises penetrating a plurality of tissue-penetrating electrode elements through the tissue surface.

53. A method as in claim 52, wherein the plurality of tissue-penetrating electrode elements are penetrated over an area in the range from 2 $cm^2$ to 10 $cm^2$.

54. A method as in claim 53, wherein the electrode elements are penetrated to a depth in the range from 3 mm to 10 mm.

55. A method as in claim 52, wherein the tissue-penetrating electrode elements are pins having a diameter in the range from 1 mm to 3 mm and a depth from an electrode face in the range from 3 mm to 10 mm.

56. A method as in claim 42, wherein high frequency current is applied simultaneously through both the array electrodes and the second electrode attached to a common pole of a power supply in a monopolar mode.

57. A method as in claim 42, wherein high frequency current is applied with one pole attached to the array electrodes and another pole attached to the second electrode in a bipolar fashion.

58. A method as in claim 42, wherein the high frequency current is applied successively from the electrodes in a monopolar mode.

59. A method as in claim 43, wherein the high frequency current is applied first through the first array of electrodes to necrose tissue at or near a boundary of the target region to inhibit blood flow into the target region.

60. A method as in claim 43 or 44, wherein the cover comprises a rigid plate.

61. A method as in claim 43 or 44, wherein the cover comprises a conformable surface.

62. A method as in claim 43 or 44, wherein the cover is composed of an electrically non-conductive material.

63. A method as in claim 43 or 44, wherein the cover and first electrode array are drawn together with a force of at least 0.5 psi.

64. A method as in claim 43 or 44, wherein deploying the first electrode array comprises positioning a probe so that a portion of the probe lies near the target region and deploying the cover comprises securing the cover to the probe after the probe has been deployed.

65. A method for treating a target region in tissue at or beneath a tissue surface, said method comprising:

deploying a first array of electrodes in the tissue at the target region;

deploying a cover composed of an electrically non-conductive material over the tissue surface over the target region, wherein the first array and cover are drawn together to apply compression on tissue in the target region; and applying electrical current to tissue in the target region through the first array of electrodes.

66. A method for treating a target region in tissue at or beneath a tissue surface, said method comprising:

deploying a first array of electrodes in the tissue at the target region;

deploying a cover composed of an electrically non-conductive material over the tissue surface over the target region, wherein the cover is configured to electrically and thermally isolate the target region and first electrode array from external tissue structures adjacent to the target region; and applying electrical current to tissue in the target region through the first array of electrodes.

67. A method as in claim 65 or 66, wherein deploying the first array of electrodes comprises:

positioning a probe so that a portion of the probe is near the target region in the tissue; and advancing a plurality of at least three array electrodes radially outwardly from the probe to define the first electrode array.

68. A method as in claim 67, wherein the probe is advanced directly into tissue with the array electrodes retracted within the probe.

69. A method as in claim 67, wherein a combination of probe and stylet is initially advanced into the tissue, and wherein the stylet is withdrawn from the probe prior to advancing the array electrodes through the probe.

70. A method as in claim 67, wherein advancing the array electrodes comprises advancing them forwardly from a distal end of the probe so that the electrodes evert outwardly as they are advanced into the tissue.

71. A method as in claim 67, wherein the array electrodes deploy outwardly to a radius from 0.5 cm to 3 cm wherein fully distally extended.

72. A method as in claim 66 or 67, wherein the first array electrodes are deployed at a depth below the tissue surface in the range from 2 cm to 10 cm.

73. A method as in claim 67, further comprising removably attaching the second electrode to the probe after the array electrodes have been advanced.

74. A method as in claim 65, wherein an high frequency current is applied first through the first array of electrodes to necrose tissue at or near a boundary of the target region to inhibit blood flow into the target region.

75. A method as in claim 65 or 66, wherein the cover comprises a rigid plate.

76. A method as in claim 65 or 66, wherein the cover comprises a conformable surface.

77. A method as in claim 65 or 66, wherein the cover and first electrode array are drawn together with a force of at least 0.5 psi.

78. A method as in claim 65 or 66, wherein deploying the first electrode array comprises positioning a probe so that a portion of the probe lies near the target region and deploying the cover comprises securing the cover to the probe after the probe has been deployed.

79. A method for treating a target region in tissue at or beneath a tissue surface, said method comprising:

deploying a first array of electrodes from a probe in the tissue at the target region so that a portion of the probe lies near the target region;

securing a cover to the probe after the probe has been deployed so that the probe lies over the tissue surface over the target region, wherein the first array and cover are drawn together to apply compression on tissue in the target region; and applying electrical current to tissue in the target region through the first array of electrodes.

80. A method for treating a target region in tissue at or beneath a tissue surface, said method comprising:

deploying a first array of electrodes from a probe in the tissue at the target region so that a portion of the probe lies near the target region;

securing a cover to the probe after the probe has been deployed so that the probe lies over the tissue surface over the target region, wherein the cover is configured to electrically and thermally isolate the target region and first electrode array from external tissue structures adjacent to the target region; and applying electrical current to tissue in the target region through the first array of electrodes.

81. A method as in claim 79 or 80, wherein deploying the first array of electrodes comprises:

positioning a probe so that a portion of the probe is near the target region in the tissue; and advancing a plurality of at least three array electrodes radially outwardly from the probe to define the first electrode array.

82. A method as in claim 81, wherein the probe is advanced directly into tissue with the array electrodes retracted within the probe.

83. A method as in claim 81, wherein a combination of probe and stylet is initially advanced into the tissue, and wherein the stylet is withdrawn from the probe prior to advancing the array electrodes through the probe.

84. A method as in claim 81, wherein advancing the array electrodes comprises advancing them forwardly from a distal end of the probe so that the electrodes evert outwardly as they are advanced into the tissue.

85. A method as in claim 81, wherein the array electrodes deploy outwardly to a radius from 0.5 cm to 3 cm wherein fully distally extended.

86. A method as in claim 79 or 80, wherein the first array electrodes are deployed at a depth below the tissue surface in the range from 2 cm to 10 cm.

87. A method as in claim 81, further comprising removably attaching an second electrode to the probe after the array electrodes have been advanced.

88. A method as in claim 79, wherein the high frequency current is applied first through the first array of electrodes to necrose tissue at or near a boundary of the target region to inhibit blood flow into the target region.

89. A method as in claim 79 or 80, wherein the cover comprises a rigid plate.

90. A method as in claim 79 or 80, wherein the cover comprises a conformable surface.

91. A method as in claim 79 or 80, wherein the cover is composed of an electrically non-conductive material.

92. A method as in claim 79 or 80, wherein the cover and first electrode array are drawn together with a force of at least 0.5 psi.

* * * * *